United States Patent [19]

Marangoni

[11] Patent Number: 5,421,341
[45] Date of Patent: Jun. 6, 1995

[54] BLOOD PRESSURE MEASURING DEVICE

[76] Inventor: Daniele Marangoni, Via Fantoli 16/15, I-20138 Milan, Italy

[21] Appl. No.: 22,777

[22] Filed: Feb. 23, 1993

Related U.S. Application Data

[63] Continuation of Ser. No. 637,982, Dec. 28, 1990, abandoned, which is a continuation of Ser. No. 287,298, Dec. 21, 1988, abandoned.

[30] Foreign Application Priority Data

Dec. 29, 1987 [EP] European Pat. Off. ............ 87119303

[51] Int. Cl.6 .................................................. A61B 5/02
[52] U.S. Cl. ..................................................... 128/677
[58] Field of Search ........................ 128/672, 677–690

[56] References Cited

U.S. PATENT DOCUMENTS

| | | |
|---|---|---|
| 2,714,379 | 8/1955 | Raines et al. . |
| 4,216,779 | 8/1980 | Squires et al. . |
| 4,248,242 | 2/1981 | Tamm ............................. 128/680 X |
| 4,269,193 | 5/1981 | Eckerle ................................ 128/672 |
| 4,300,573 | 11/1981 | Rebbe et al. . |
| 4,469,107 | 9/1984 | Asmar et al. ........................ 128/681 |
| 4,549,550 | 10/1985 | Kaml ................................... 128/686 |
| 4,706,684 | 11/1987 | Sorenson et al. ............... 128/686 X |
| 4,821,517 | 4/1989 | Zarotti ................................. 60/531 |

FOREIGN PATENT DOCUMENTS

| | | |
|---|---|---|
| 246571 | 11/1987 | European Pat. Off. . |
| 8606603 | 11/1986 | France ............................. 128/680 |
| 3613889 | 10/1987 | Germany . |
| 2191587 | 12/1987 | United Kingdom . |

*Primary Examiner*—Lee S. Cohen
*Assistant Examiner*—John P. Lacyk

[57] ABSTRACT

A blood pressure measuring device having a blood occluding cuff for surrounding a patient's arm in which a pump for inflating the cuff, a valve for deflating the cuff, a pressure transducer for measuring cuff pressure all are located on the cuff, and in which an electrical control and pressure signal processing device communicates with the cuff only by an electrical connection.

6 Claims, 1 Drawing Sheet

5,421,341

BLOOD PRESSURE MEASURING DEVICE

This a continuation of application Ser. No. 07/637,982, filed on Dec. 28, 1990, now abandoned which is a continuation of Ser. No. 07/287,298, filed on Dec. 21, 1988, now abandoned.

BACKGROUND OF THE INVENTION

1. Field of the Invention

The invention relates to an improved blood pressure monitoring device in which the pump, valve and transducer are located on the cuff which surrounds a patient's arm.

2. Description

Automatic blood pressure measuring devices for measuring a patient's blood pressure in certain intervals over an extended period of time or upon manual initiation by the patient or the medical staff are known for a long time either for stationary or ambulatory purposes. For ambulatory use it is necessary that the device is small and lightweight and contains a data storage system. A further major requirement for all blood pressure measuring devices is the reduction or elimination of artefacts due to relative movement between patient and recording device.

In all blood pressure measuring devices known up till now a cuff surrounding the patient's arm is connected via a hose to a module containing the pressurizing system and the signal processing circuitry. In the classical embodiment a second hose is connected between a transducer which is also contained in the module and the cuff to measure the cuff pressure. A valve is connected to the pressurizing system between the pump and cuff.

According to a more recent development the pressure transducer is also connected to the pressurizing system between the pump and the cuff so that the second hose could be eliminated. Still the connection between the module and the cuff is affected by the hose supplying or withdrawing the air or gas for inflating or deflating the cuff.

It has been discovered that this configuration causes considerable artefacts resulting in inaccurate or unstable readings due to the movement of the hose in case of relative movement of the patient with regard to the module. A further disadvantage resides in the significant portion of dead volume which has to be pressurized during inflation of the cuff and which requires oversized pumps.

The present invention provides a blood pressure measuring device for ambulatory purpose which generates less artefacts and exhibits a lower dead volume than the devices known to date.

SUMMARY OF THE INVENTION

This invention relates to a blood pressure measuring device having a blood occluding cuff for surrounding a patient's arm, a pump for inflating the cuff, a valve for deflating the cuff, a pressure transducer for deriving electrical signals indicative of the cuff pressure and electrical controlling and signal processing means for controlling the cuff function and for processing the derived pressure signals.

In the invention, the pump, the valve and the transducer are located in the cuff and only an electrical connection exists between the cuff and the electrical control and signal processing means.

BRIEF DESCRIPTION OF THE DRAWINGS

A preferred embodiment of the invention is described in connection with the accompanying drawings wherein.

DETAILED DESCRIPTION OF A PREFERRED EMBODIMENT

Figure 1:
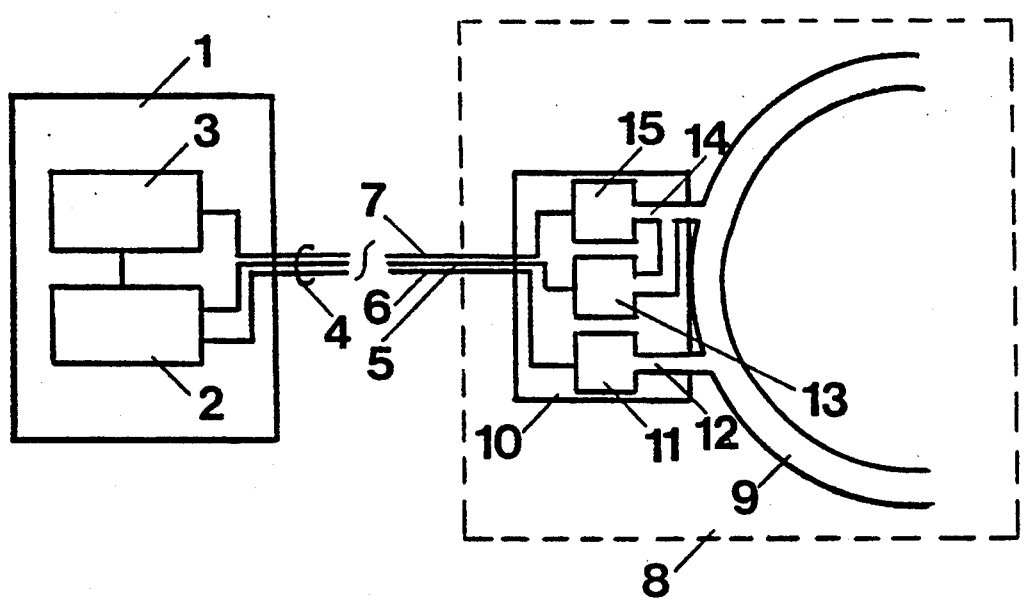
FIG. 1 is a block diagram and a schematic cross-section of a system according to the invention and FIG. 2 is a cross section of an embodiment of a cuff according to the present invention.

The schematic block diagram of FIG. 1 shows a control and signal processing device or module 1 containing a pressurizing control circuit 2 and a signal processing circuit 3. Both, pressurizing control circuitry and signal processing circuitry for blood pressure measuring devices are well known in the art and are not described in detail here.

The module 1 is connected by a cable 4 with a cuff 8. The cuff 8 is shown in a schematic cross section in FIG. 1 and contains a bag or bellows 9 for exerting pressure on a patient's arm and a housing 10 for encasing active components. The housing 10 contains a pump 11 which is connected by a short tube 12 to bag 9. The pump may be a pneumatic membrane pump such as are commercially available as so-called "micro compressors", having the electronics for controlling a chemical which expands upon electrical activation to inflate the cuff. Pump 11 is activated by current supply via an electrical conductor 5 connecting the pump with the control circuit 2. When activated, pump 11 inflates the bag 9 to a certain predetermined pressure as described below and then is inactivated.

Housing 10 further contains a valve 13 which is also connected to bag 9 by a tubing 14. Valve 13 is electrically connected via an electrical conductor 6 to control circuit 2. Valve 13 is a solenoid valve which is electrically activated to close or open a pressure outlet from the bag 9 to the ambient air.

Equally connected to tube 14 is a pressure transducer 15 which senses the pressure in the tubing 14 and thus in the bag 9 and generates a signal representative of the sensed pressure. The transducer 15 is connected via an electrical conductor 7 to signal processing circuit 3 in module 1. In the processing circuit 3 the pressure signal serves two purposes. Firstly, it is processed to discriminate between diastolic and systolic pressure from the derived signals. These pressure values are recorded in the usual manner. For this purpose the module 1 contains a conventional recorder (not shown).

The second function of the signals received from the transducer is to generate control signals to inactivate or terminate the pump action of pump 11 at the end of the inflation period and for opening and closing the valve 13. The entire inflating and deflating cycle is initiated by a suitable clock (not shown) contained in the control circuit 2. The intervals which are provided by this clock for initiating the pressure cycles may preferably be set by the patient or the medical staff from the outside.

Figure 2:
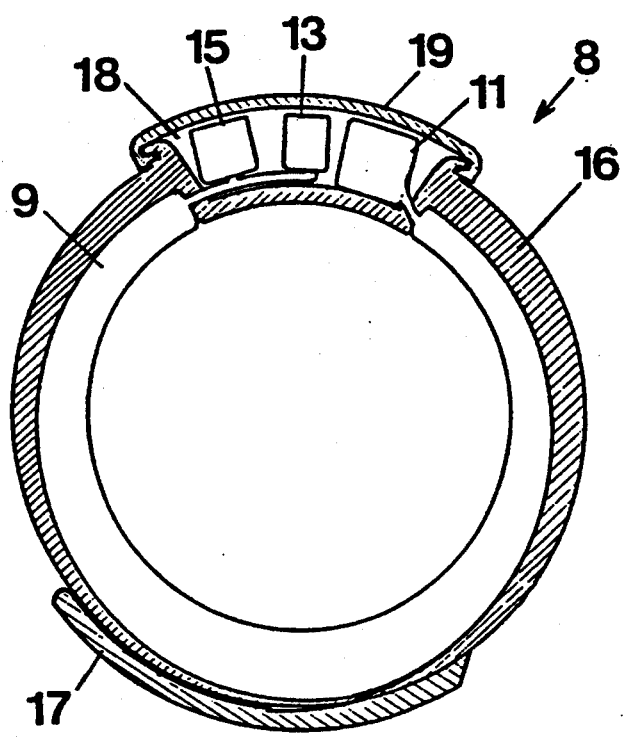

FIG. 2 shows a cross sectional diagram of an actual configuration of the cuff 8. The housing 10 for the active components is constituted by a semi-rigid element 16 which has an essentially cylindrical shape which is open at its lower side and is provided with a closing element 17 over this open portion. On the side opposite to the opening the semi-rigid element 16 is provided with a chamber 18 which is covered by a lid 19. The chamber 18 and the lid 19 together constitute the housing 10.

Along the inner side of the cylindrical semi-rigid element 16 an inflatable bag 9 is arranged. The bag 9 is so configured that it covers the inner surface of the semi-rigid element 16. The bag has two openings to which tubes 12 and 14 are sealidly connected. Inside the chamber 18 are shown the pump 11 connected to tube 12 on one side. On the other side of chamber 18 there is valve 13 and transducer 15 connected to tube 14.

An advantage of this embodiment of the cuff is the fact that it can be applied to and closed upon the arm by one hand, i.e. by the patient himself. A further advantage of the combination of a semi-rigid element and an inflatable bag is a lower dead volume than with conventional cuffs.

For blood pressure measurement or monitoring the cuff is opened on its lower side to expand its diameter such that it can be put over a patient's arm. As soon at it is positioned at the measuring site the closure means 17 is closed and the inflation/deflation may be initiated. Pump 11 inflates the bag 9 which exerts pressure on the arm. During the increase of pressure an electrical pressure signal generated by the transducer is monitored to determine the pulse waves which are superposed to the raising pressure value. In this way the diastolic and the systolic pressure can be determined in the usual manner. After the cuff pressure has increased above systolic pressure a signal is generated to open valve 13 to deflate the cuff to the initial state. Thereafter a further cycle can be initiated either immediately or after a predetermined period of time.

An advantageous side effect of the invention is the fact that due to the change of location of the pump more space is available in the recording device without increasing its dimensions. This space can be used for adding memory and computer capabilities to simultaneously analyze the electrocardiogram of the patient.

Within the scope of the invention the pump and/or the valve of the improved blood pressure measuring device can comprise pneumatic, electrical, electronic, mechanical or chemical means for inflating and deflating the cuff and for controlling the inflation and deflation of the cuff.

I claim:

1. An automatic blood pressure measuring device for measuring a patient's blood pressure comprising a blood occluding cuff for surrounding a patient's arm and a module electrically coupled to the cuff wherein the only coupling between the cuff and the module consists of an electrical coupling; the cuff containing a housing enclosing a pump which pneumatically communicates with the cuff for inflating the cuff, a valve pneumatically communicating with the cuff for deflating the cuff and a pressure transducer communicating with the cuff for deriving electrical signals indicative of cuff pressure; the module electrically coupled to the cuff comprising an electrical controlling and signal processing means for remotely controlling the cuff pressure and for processing derived pressure signals wherein the valve is electrically activated to close or open by the remote controlling and processing means and wherein the pump is electronically activated to inflate the cuff and deactivated to allow cuff deflation by the remote controlling and processing means.

2. The device of claim 1, wherein the valve comprises electrical means for inflating and deflating the cuff and for controlling the inflation and deflation of the cuff.

3. The device of claim 1, wherein the valve comprises electronic means for inflating and deflating the cuff and for controlling the inflation and deflation of the cuff.

4. A blood pressure measuring device according to claim 1, wherein said module includes an electrocardiogram recording and analyzing system.

5. The device according to claim 1 in which said module includes a clocking circuit for automatically initiating cuff pressurization.

6. The device according to claim 1 in which said pump comprises a bladder activated by current from said module.

* * * * *